United States Patent
Bonner et al.

(10) Patent No.: US 7,985,948 B2
(45) Date of Patent: Jul. 26, 2011

(54) SYSTEMS AND METHODS FOR ANALYZING SUBSTANCES USING A MASS SPECTROMETER

(75) Inventors: Ron F. Bonner, Newmarket (CA); Lyle L. Burton, Woodbridge (CA); Yves Le Blanc, Toronto (CA)

(73) Assignee: DH Technologies Development Pte. Ltd., Singapore (SG)

( * ) Notice: Subject to any disclaimer, the term of this patent is extended or adjusted under 35 U.S.C. 154(b) by 414 days.

(21) Appl. No.: 12/326,241

(22) Filed: Dec. 2, 2008

(65) Prior Publication Data

US 2009/0140139 A1    Jun. 4, 2009

Related U.S. Application Data

(60) Provisional application No. 60/992,172, filed on Dec. 4, 2007.

(51) Int. Cl.
*H01J 49/00* (2006.01)

(52) U.S. Cl. ........ 250/281; 250/282; 250/287; 250/288; 250/289; 436/173

(58) Field of Classification Search .................. 250/281, 250/282, 287, 288, 289; 436/173
See application file for complete search history.

(56) References Cited

U.S. PATENT DOCUMENTS

| | | | |
|---|---|---|---|
| 6,624,408 B1 * | 9/2003 | Franzen | ........................ 250/282 |
| 6,744,040 B2 | 6/2004 | Park | |
| 6,744,043 B2 | 6/2004 | Loboda | |
| 6,940,065 B2 | 9/2005 | Graber et al. | |
| 7,009,174 B2 | 3/2006 | Le Blanc | |
| 2006/0284080 A1 | 12/2006 | Makarov et al. | |
| 2007/0096021 A1 * | 5/2007 | LeBlanc et al. | ................ 250/282 |

OTHER PUBLICATIONS

Kevin G. Owens, "Application of Correlation Analysis Techniques to Mass Spectral Data" Applied Spectroscopy Reviews, vol. 27 (1), pp. 1-49 (1992).
G.M Hieftje, R.I, Bystroff and Roberty Liam, "Application of Correlation Analysis for Signal-to-Noise Enhancement in Flame Spectrometry", Analytical Chemistry, vol. 45, No. 2, pp. 253-258 (Feb. 1973).
R. B. Lam, D. T. Sparks and T. L. Isenhour, "Cross-Correlation Signal/Noise Enhancement with Applications to quantitative Gas Chromatography/Fourier Transform Infrared Spectrometry", Analytical Chemistry, vol. 54, pp. 1927-1931 (1982).
Written Opinion and International Search Report. Application No. PCT/CA2008/002083. Dated Mar. 9, 2009.

* cited by examiner

*Primary Examiner* — Robert Kim
*Assistant Examiner* — Michael Maskell
(74) *Attorney, Agent, or Firm* — John R. Kasha; Kasha Law LLC

(57) ABSTRACT

Systems and methods for analyzing compounds in a sample. In one embodiment, the present technology is directed towards a method of analyzing a sample, comprising: emitting ions from the sample; selecting the emitted ions for a designated ion; fragmenting the designated ions; scanning for a plurality of designated ion fragments; determining a designated fragment chromatographic trace for each designated ion fragment; and generating a combined chromatographic trace corresponding to a non-linear combination of a plurality of designated fragment chromatographic traces.

24 Claims, 5 Drawing Sheets

| PRECURSOR ION M/Z | FRAGMENT M/Z | SCANNING WINDOW |
|---|---|---|
| 158 | 24 | 0.0 min. - 1.5 min. |
|  | 17 |  |
|  | 180 |  |
| 103 | 42 | 0.5 min. - 3.5 min. |
|  | 33 |  |
|  | 73 |  |
| 163 | 10 | 21.0 min. - 24.0 min. |
|  | 18 |  |
|  | 26 |  |
| ... | ... | ... |

Fig. 2

SYSTEMS AND METHODS FOR ANALYZING SUBSTANCES USING A MASS SPECTROMETER

PRIORITY

The present application claims priority from U.S. provisional patent application No. 60/992,172, filed Dec. 4, 2007, which is incorporated herein by reference in its entirety.

FIELD

The present application relates generally to the field of mass spectrometry.

BACKGROUND

The analysis of a substance to determine its composition may be necessary for many applications, including toxicology, forensics and environmental testing, as well as food and drug research. Often, samples to be analyzed are analyzed for the presence of numerous different analytes of interest. Such samples may, for example, be in the form of bodily fluids taken from test subjects, which fluids often include both drug metabolites of interest, as well as irrelevant endogenous ions from the test subject. Within complex samples, correctly determining the presence or absence as well as the quantities of a large number of analytes of interest, can be difficult and time-consuming.

Mass spectrometers are often used for producing a mass spectrum of a sample to find its composition. This is normally achieved by ionizing the sample and separating ions of differing masses and recording their relative abundance by measuring intensities of ion flux. For example, with time-of-flight mass spectrometers, ions are pulsed to travel a predetermined flight path. The ions are then subsequently recorded by a detector. The amount of time that the ions take to reach the detector, the "time-of-flight", may be used to calculate the ion's mass to charge ratio, m/z.

Additional information (in addition to an ion's precursor mass) can then be obtained by fragmenting the ion via CID (collision induced dissociation) in a collision cell (or other means) to generate an MSMS spectrum. In most instruments with MSMS capabilities, the process of generating a mass spectrum, selecting a precursor ion and generating an MSMS (mass spectrum/mass spectrum) spectrum can be performed in an automated mode. This mode of acquisition is frequently referred to as Information Dependant Acquisition (IDA) or Data Dependant Experiment (DDE).

Chromatographic equipment such as a liquid chromatograph may be used to elute or release ions from a sample into the mass spectrometer over a period of time. Multiple reaction monitoring (MRM) or other techniques may be used to analyze the ions received by the mass spectrometer.

For complex samples, LC/MS quantitation techniques using MRM frequently involve interfering matrix components exhibiting the same Q1 and Q3 masses as the analytes of interest. As a result, it may be difficult to determine which peak in a chromatogram represents the particular analyte of interest. There may also be small changes in retention time that increase the difficulty of peak finding. When dealing with a small number of analytes, this problem can usually be addressed by using specific sample cleanup techniques, isotopically enriched versions of the analytes as internal standards, or even sufficient manual intervention. For large numbers of analytes, however, such solutions are impractical.

The applicants have accordingly recognized a need for systems and methods for analyzing and identifying ions from samples.

SUMMARY

In one aspect, the present technology is directed towards a system for analyzing analytes in a sample. The system includes an ion source for emitting ions from the sample, a mass spectrometer adapted to receive the ions from the ion source, a controller operatively coupled to the mass spectrometer and configured to control the first mass analyzer to analyze for a designated ion of interest and to control the second mass analyzer to analyze for a designated ion fragment of interest. The system also includes data storage for storing at least one analyte parameter set, wherein each analyte parameter set includes: a designated precursor ion, a plurality of designated ion fragments, and a retention time window.

The mass spectrometer includes a first mass analyzer to select ions received from the ion source, an ion fragmenter configured to fragment ions received from the first mass analyzer, a second mass analyzer configured to select ion fragments received from the ion fragmenter, and at least one detector configured to detect ion fragments received from the second mass analyzer.

The controller is responsive to the analyte parameter set, and during the retention time window for each analyte parameter set the controller is configured to control the first mass analyzer to select for the corresponding designated precursor ion and to control the second mass analyzer to select for the corresponding designated ion fragments. The controller is configured to determine a chromatographic trace for each designated ion fragment in the analyte parameter set and wherein the controller is configured to determine a combined chromatographic trace corresponding to a non-linear combination of a plurality of designated fragment chromatographic traces for the analyte parameter set.

Each chromatographic trace may comprise a plurality of data points, each data point corresponding to an intensity of ion fragments detected by the detector at a point in time, and the controller may be configured to determine the combined chromatographic trace for an analyte set by, for each point in time during the corresponding retention time window, multiplying the values of each corresponding data point in each chromatographic trace.

In another aspect, the technology is directed towards a system for analyzing ions emitted from an ion source. The system includes a first mass analyzer adapted to receive and to select ions from the ion source, an ion fragmenter configured to fragment ions received from the first mass analyzer, a second mass analyzer configured to select ion fragments received from the ion fragmenter, and a detector configured to detect ion fragments received from the second mass analyzer.

The system also includes a controller operatively coupled to the first and second mass analyzers, to the fragmenter and to the detector, wherein the controller is configured to control the first mass analyzer to analyze for a designated ion of interest and to control the second mass analyzer to select for a designated ion fragment of interest. The system further includes data storage for storing at least one analyte parameter set, wherein each analyte parameter set includes a designated precursor ion, a plurality of designated ion fragments, and a retention time window.

The controller is responsive to the analyte parameter set, and during the retention time window for each analyte parameter set the controller is configured to control the first mass analyzer to select for the corresponding designated precursor ion and to control the second mass analyzer to select for the corresponding designated ion fragments. The controller is further configured to determine a chromatographic trace for each designated ion fragment in the analyte parameter set and the controller is configured to determine a combined chromatographic trace corresponding to a non-linear combination of a plurality of designated fragment chromatographic traces.

Each chromatographic trace may comprise a plurality of data points, each data point corresponding to an intensity of ion fragments detected by the detector at a point in time, and the controller may be configured to determine the combined chromatographic trace for an analyte set by, for each point in time during the corresponding retention time window, multiplying the values of each corresponding data point in each chromatographic trace.

In yet a further aspect, the present technology is directed towards a method of analyzing a sample, comprising: emitting ions from the sample; selecting the emitted ions for a designated ion; fragmenting the designated ions; scanning for a plurality of designated ion fragments; determining a designated fragment chromatographic trace for each designated ion fragment; generating a combined chromatographic trace corresponding to a non-linear combination of a plurality of designated fragment chromatographic traces.

In some embodiments, the process of generating a combined chromatographic trace comprises multiplying the designated fragment chromatographic traces together to generate the combined chromatographic trace.

The method may further comprise generating a report containing data corresponding to the determined retention time.

In another aspect, the invention may be directed to computer readable media configured to cause a mass spectrometer having a computer controller to perform the method.

BRIEF DESCRIPTION OF THE DRAWINGS

The present invention will now be described, by way of example only, with reference to the following drawings, in which like reference numerals refer to like parts and in which:

FIG. 2 is a is a representative example of analyte parameter data as may be stored in the data storage of the mass spectrometer of FIG. 1;

DETAILED DESCRIPTION

Figure 1:
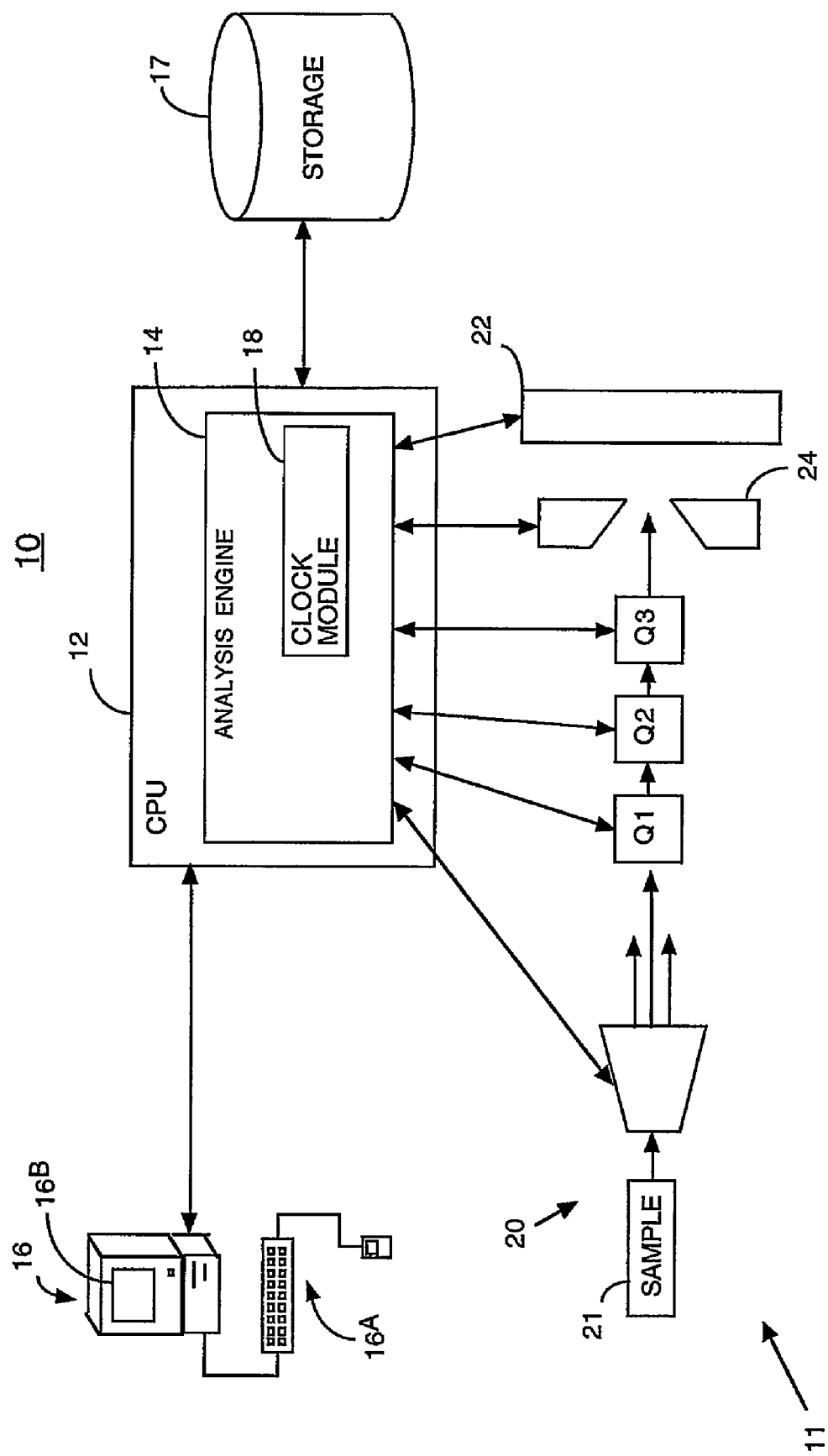
FIG. 1 is a schematic diagram of a mass spectrometer made in accordance with the present disclosure.

Referring to FIG. 1, illustrated therein is an analysis system referred to generally as 10, made in accordance with the present disclosure. The system 10 is configured to be capable of performing scheduled MRM in accordance with the present disclosure, as will be understood.

The analysis system 10 includes a mass spectrometer 11 (which may be an MS/MS system such as a hybrid quadrupole time-of-flight or triple quadrupole system. The spectrometer 11 comprises a suitably programmed controller or central processing unit (CPU) 12 having a suitably programmed analysis engine 14 stored in RAM or other suitable computer-readable media. Alternatively, the engine 14 may reside on a CPU remote from the CPU 12, for remote processing of the data. An input/output (I/O) device 16 (typically including an input component $16^A$ such as a keyboard or control buttons, and an output component such as a display $16^B$) is also operatively coupled to the CPU 12. Data storage 17 is also provided.

The system 10 also includes an ion source 20, configured to emit ions, generated from the sample 21 to be analyzed. The ion source 20 may be a continuous ion source, for example, such as an electron impact or chemical ionization source (which may be used in conjunction with a gas chromatography source), or an electrospray or atmospheric pressure chemical ionization ion source (which may be used in conjunction with or operatively coupled to a liquid chromatography source), or a desorption electrospray ionization (DESI), or a laser desorption ionization source, as will be understood.

The ion source 20 can also be provided with an ion transmission ion guide, such as a multipole ion guide, ring guide, or an ion mass filter, such as a quadrupole mass filter, or an ion trapping device, as generally known in the art (not shown). For brevity, the term ion source 20 has been used to describe the components which generate ions from the sample 21, and emit analyte ions of interest for detection. Other types of ion sources 20 may also be used, such as a system having a tandem mass filter and ion trap. Preferred ion sources are those which emit the ions from the sample 21 over a range of times, to enable mass analysis by the mass spectrometer 11 using MRM or other suitable techniques.

As will be understood, liquid chromatography may be used to separate compounds dissolved in solvent from other substances in the sample 21, and release or emit such compounds for MS analysis. As a result of the different timings for the chemical interactions that take place during the LC phase, the analytes of interest are released over time. The release times for specific analytes can be estimated, based on the expected chemical interactions.

As noted above, the spectrometer 11 may comprise a triple quadrupole mass spectrometer, having triple rod sets Q1, Q2 and Q3. The rod sets Q1 and Q3 may be controlled by the processor 12 (via the trigger engine 14) to select or filter for ions having a particular m/z. In contrast, the Q2 rod set is provided with a chamber and configured to operate as a collision cell or fragmenter for fragmenting the ions received from Q1. The resulting ion fragments may be passed through to, and selectively filtered by, rod set Q3, before being detected or recorded by the detector 22.

Optics 24 or other focusing elements, such as an electrostatic lens can also be disposed in the path of the emitted ions, typically between the Q3 rod set and the detector 22, for focusing the ions onto the detector 22.

Figure 2:
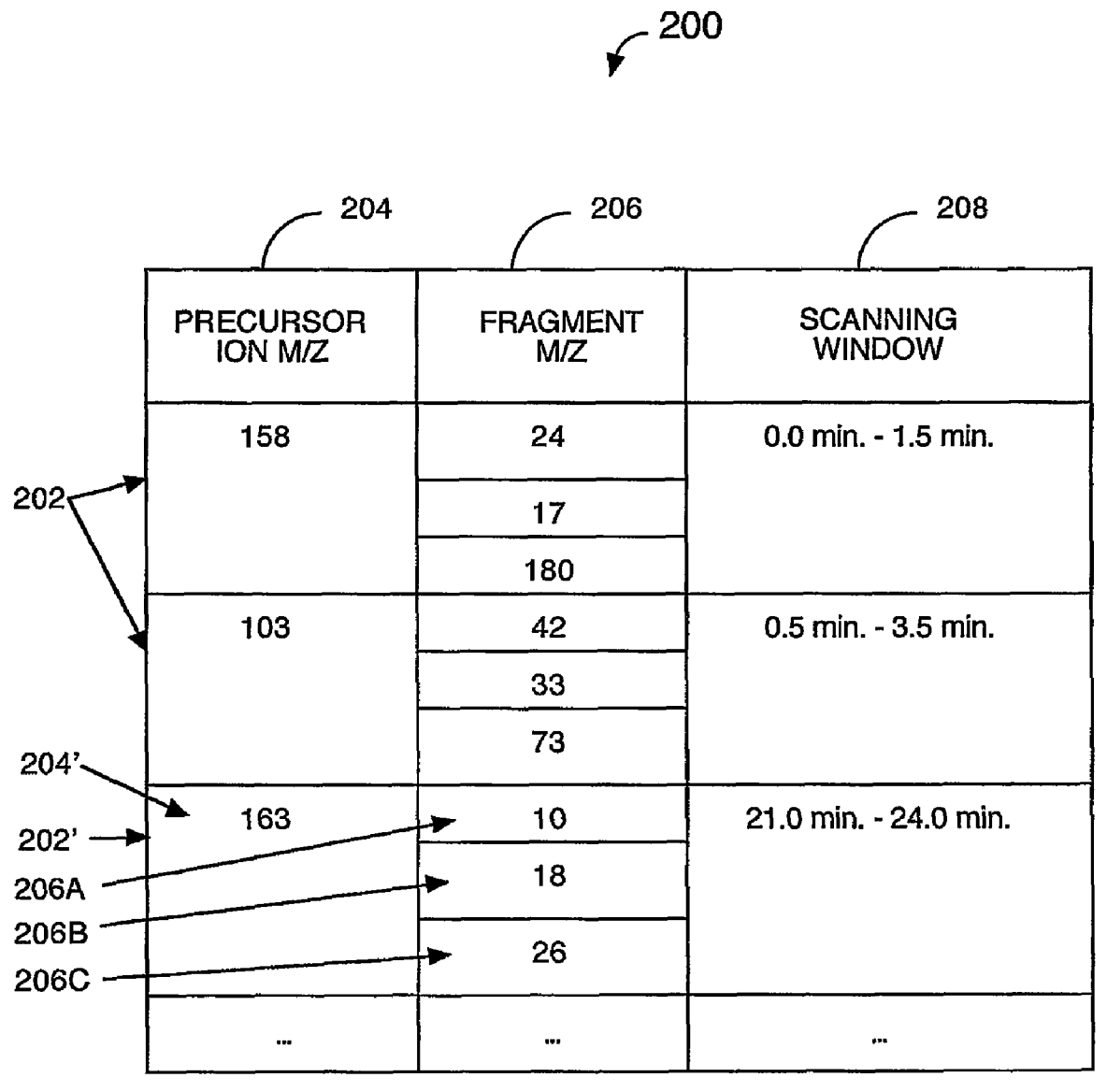

Referring now to FIG. 2, illustrated therein is a representative example of analyte parameter data 200 as may be stored in the data storage 17. The analyte parameter data 200 includes at least one analyte parameter set 202, and each analyte parameter set 202 includes: a m/z value corresponding to a designated precursor ion 204, a plurality of m/z values corresponding to designated ion fragments 206, and timing data corresponding to a retention time window 208. While the example data is illustrated with having three ion fragments 206 per parameter set 202, it should be understood that different numbers of fragments 206 may be determined for each set 202. As will also be understood, the retention time window 208 corresponds to a predetermined period of time when the corresponding precursor ion 204 is expected to be emitted by the ion source 20 from the sample 21. It should also be understood that the retention time or scanning window data 208 is not a requirement, since for certain simplified applications, the "windows" may be treated as running for the entire analysis period.

Figure 3A:
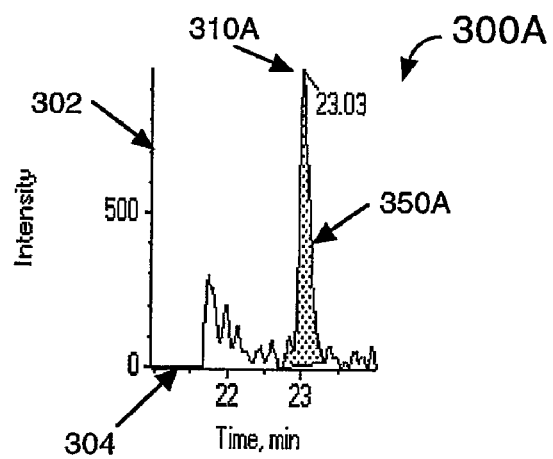
FIG. 3A is a representative example of a chromatographic trace corresponding to a first designated ion fragment in a parameter set of FIG. 2.
Figure 3B:
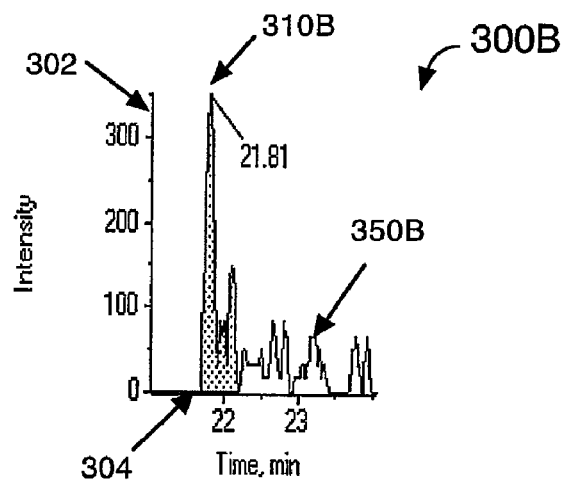
FIG. 3B is a representative example of a chromatographic trace corresponding to a second designated ion fragment in a parameter set of FIG. 2.
Figure 3C:
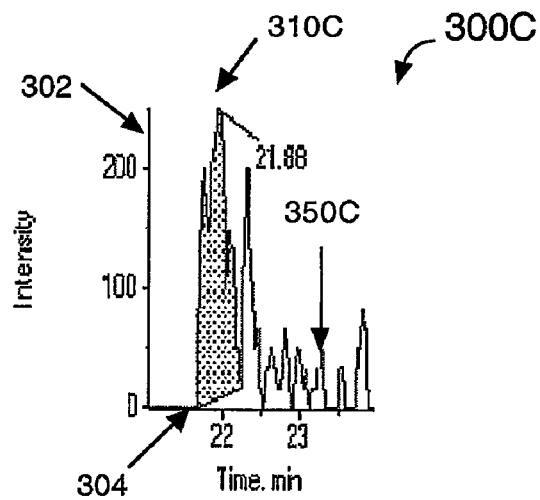
FIG. 3C is a representative example of a chromatographic trace corresponding to a third designated ion fragment in a parameter set of FIG. 2.

Referring now to FIGS. 3A to 3C, illustrated therein are example chromatographic traces comprising a plurality of data points, each data point corresponding to an intensity of ion fragments detected by the detector at a point in time, as may be generated by the processing of the sample 21 for analysis by the mass spectrometer 11, as will be discussed in greater detail, below. It should be understood that charts such as those illustrated in FIGS. 3A to 3C corresponding to the designated fragment chromatographic traces may, but need not be, generated—rather, the designated fragment chromatographic trace data may simply be stored in data storage 17 and processed by the analyzer engine 14 in accordance with the present disclosure.

Illustrated in FIG. 3A is a representative example of a chromatographic trace 300A (which may be stored in data storage 17) corresponding to a first designated ion fragment 206A in the parameter set 202' discussed in relation to FIG. 2. The vertical axis 302 of the chart 300A represents the intensity of the designated ion fragments 206A detected by the detector 22. The horizontal axis 304 of the chart 300A corresponds to time and in the example the unit of measurement is minutes. In the example data, a dominant peak 310A appears at approximately 23.03 minutes.

Similarly, FIG. 3B is a representative example of a chromatographic trace 300B (which may be stored in data storage 17) corresponding to a second designated ion fragment 206B in the parameter set 202' discussed in relation to FIG. 2. The vertical axis 302 of the chart 300B represents the intensity of the designated ion fragments 206B detected by the detector 22. The horizontal axis 304 of the chart 300B corresponds to time and in the example the unit of measurement is minutes. In the example data, a dominant peak 310B appears at approximately 21.81 minutes.

Also similarly, FIG. 3C is a representative example of a chromatographic trace 300C (which may be stored in data storage 17) corresponding to a second designated ion fragment 206C in the parameter set 202' discussed in relation to FIG. 2. The vertical axis 302 of the chart 300C represents the intensity of the designated ion fragments 206C detected by the detector 22. The horizontal axis 304 of the chart 300C corresponds to time and in the example the unit of measurement is minutes. In the example data, a dominant peak 310C appears at approximately 21.88 minutes.

Figure 4:
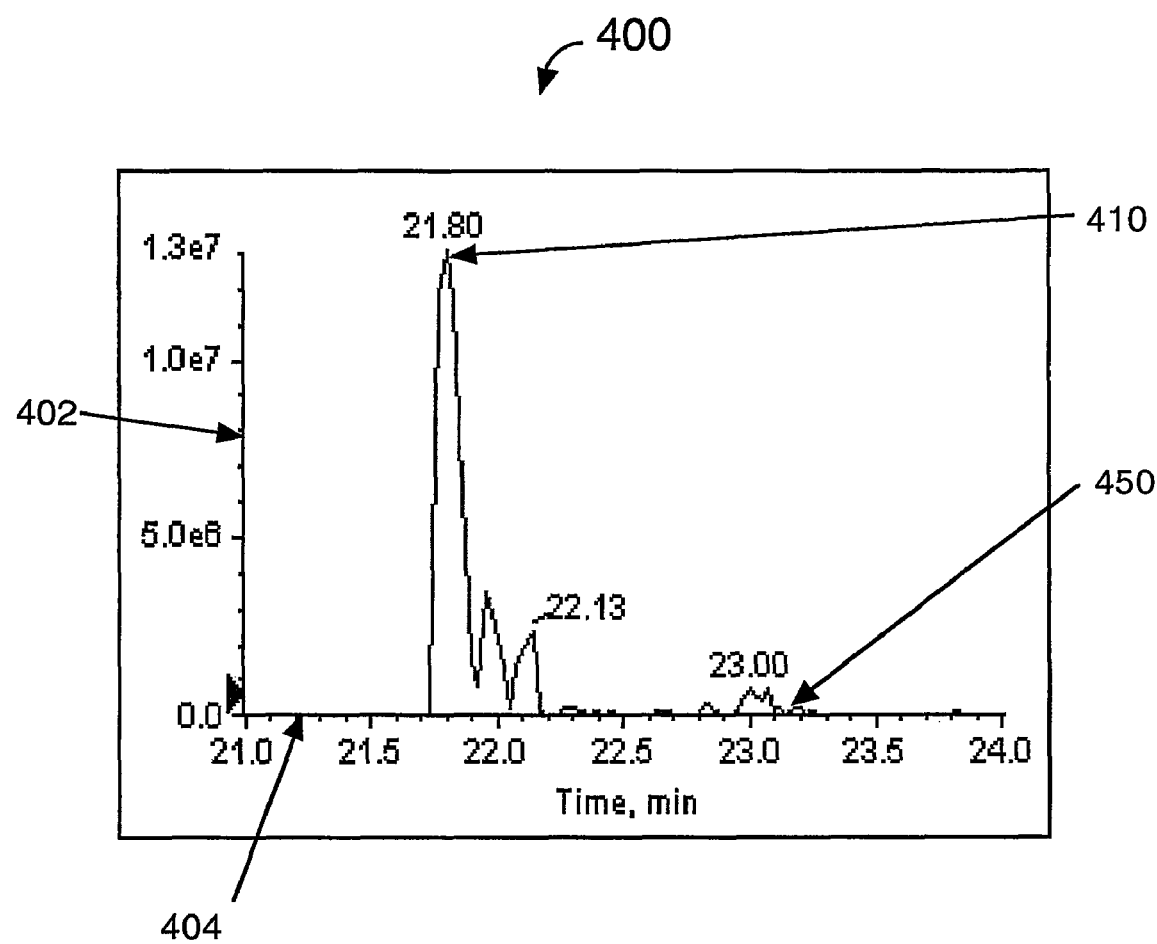
FIG. 4 is a representative example of a combined chromatographic trace in accordance with the present disclosure corresponding to a non-linear combination of the designated fragment chromatographic traces of FIGS. 3A, 3B and 3C.

Turning now to FIG. 4, illustrated therein is a representative example of a combined chromatographic trace 400 (as may be stored in the data storage 17) generated by the analysis engine 14 and corresponding to a non-linear combination of the designated fragment chromatographic traces 300A, 300B and 300C. The vertical axis 402 of the chart 400 represents the multiplied intensity values from the designated fragment chromatographic traces 300A, 300B and 300C. The horizontal axis 404 of the chart 400 corresponds to time and in the example the unit of measurement is minutes.

As will be understood, in operation, the CPU 12/analysis engine 14 is responsive to the analyte parameter data 200 and specifically to the analyte parameter sets 202 (including for example, 202'). As will be discussed in greater detail below, the engine 14 is configured to regulate the operation of the mass analyzers Q1 and Q3, to filter for the corresponding precursor ions 204 and confirmatory ion fragments 206, during the corresponding retention time windows 208 for each analyte parameter set 202. Once the designated fragment chromatographic traces (eg. 300A, 300B, 300C) have been determined for a parameter set (eg. 202'), the engine 14 is further configured to generate a combined chromatographic trace (eg. 400) which corresponds to a non-linear combination of the designated fragment chromatographic traces. The engine 14 is further configured to determine a retention time corresponding to the analyte parameter set.

Figure 5:
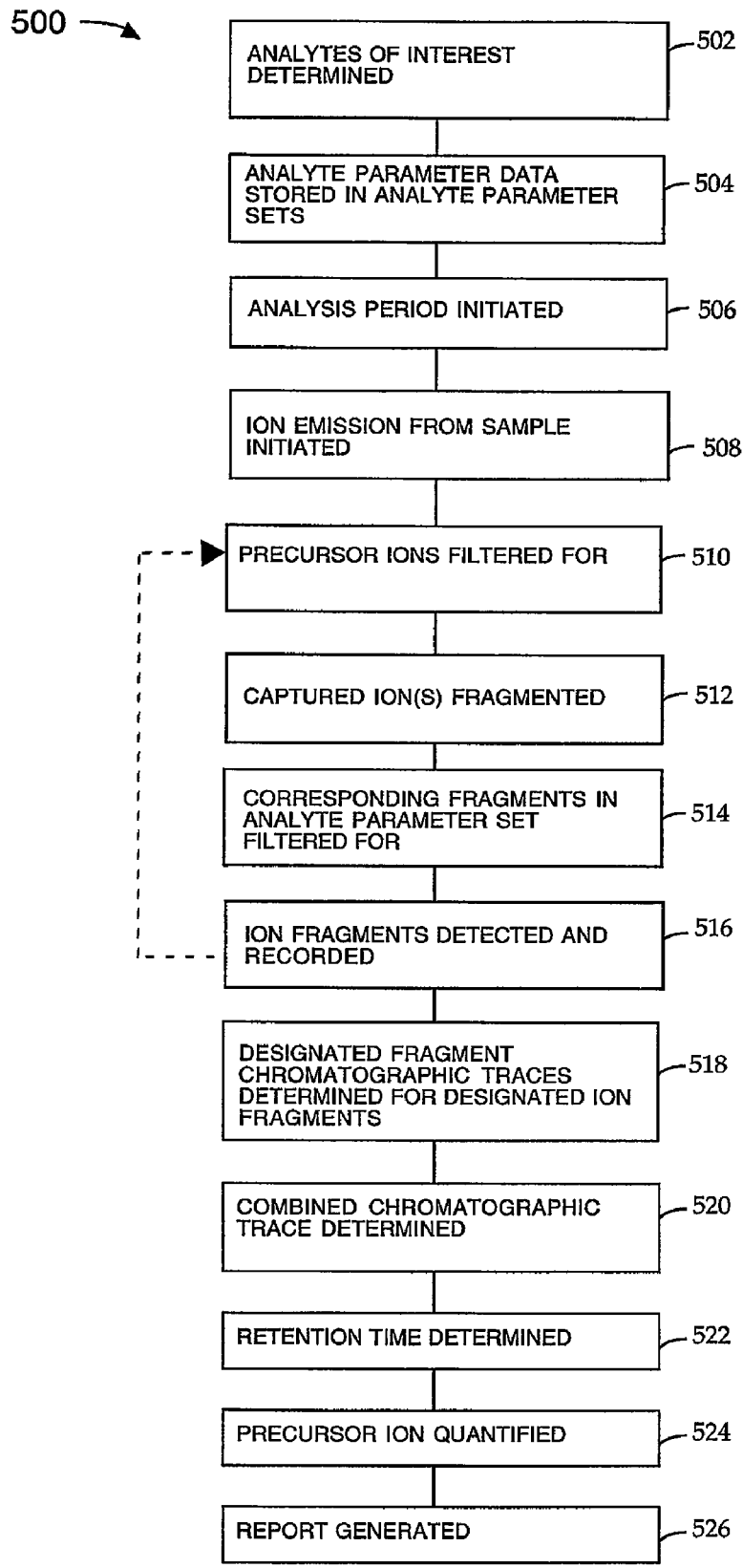
FIG. 5 is a flow diagram illustrating the steps of a method of analyzing a compound in accordance with the present disclosure.

FIG. 5 sets out the steps of the method, referred to generally as 500, carried out by the spectrometer system 10 during an analysis period. Typically, before the analysis period is commenced, the analytes of interest are determined (for which the sample 21 is being analyzed) (Block 502). Typically, for each analyte of interest, a designated precursor ion 204 and a plurality of corresponding designated ion fragments 206 are stored in analyte parameter sets 202 in the analyte parameter data 200. The corresponding retention time window 208 for each parameter set 202, is also determined and stored (Block 504).

As will be understood, the analyte parameter sets 202 (designated precursor ion 204 and designated ion fragments 206, together with the corresponding retention time window 208) for numerous analytes of interest may be previously calculated and stored as a library of data in the data storage 17, and simply indexed and retrieved by the user and the CPU 12 utilizing the I/O device 16.

The user will then typically input a command to commence an analysis period (typically via the I/O device 16), upon receipt of which the analysis engine 14 is programmed to initiate the analysis period (Block 506).

When the analysis period is commenced, the ion source 20 is activated to commence the emitting of ions from the sample 21 (which may be the commencement of the LC phase as outlined above) (Block 508). As will be understood, the sample may, for example, include bodily fluid taken from a test subject, which fluid often includes both drug metabolites of interest, as well as irrelevant endogenous ions from the test subject.

The system 10 is then configured to selectively filter the emitted ions for the designated precursor ions 204 during the corresponding retention time windows 208 (Block 510). As will be understood, the CPU 12/analysis engine 14 is programmed to cause the rod set Q1 to selectively filter the ions received from the ion source 20 for the designated precursor ions 204.

The filtered ions 204 are then received by the fragmentation module/rod set Q2 and fragmented (Block 512). The fragments are then received by the Q3 rod set, which is controlled by the analysis engine 14 to scan or filter for the corresponding designated ion fragments 206 (Block 514). Such designated ion fragments 206 (if any) are permitted to impact the detector 22. If the detector 22 detects a designated ion fragment 206 (Block 516), the analysis engine 14 is programmed to store corresponding data in the data storage 17. As will be understood, the filtering, fragmenting, filtering and detecting steps of Blocks 510-516 are typically performed substantially simultaneously for multiple analyte parameter sets 202 which happen to share overlapping retention time windows 208.

The process 500 cycles through the various steps 510-516 until the analysis period is complete and ion emission is terminated.

The analysis engine 14 determines a designated fragment chromatographic trace (eg. 300A, 300B, 300C) for a plurality of and typically each designated ion fragment 206 (Block 518). Such traces will be effected subsequent to the expiry of the retention time window 208 for a particular parameter set 202, 202' (which may be during or following the analysis period). As noted, the traces (eg. 300A, 300B, 300C) may simply comprise the collection of data points represented by the chromatographic charts illustrated in FIGS. 3A, 3B and 3C, and may not be required to be a separate step.

For each analyte parameter set 202, 202', the analysis engine 14 determines a combined chromatographic trace 400 corresponding to a non-linear combination of a plurality of the designated fragment chromatographic traces (eg. 300A, 300B, 300C) (Block 520). The analysis engine 14 may be configured to determine the combined chromatographic trace 400 for an analyte parameter set by, for each point in time during the corresponding retention time window, multiplying the values of each corresponding data point in each such designated fragment chromatographic trace (eg. 300A, 300B, 300C). Thus, for example, the value of point 450 at the time 23.17 minutes in the combined chromatographic trace 400 is determined by multiplying together the corresponding values 350A, 350B, 350C (all at the time of 23.17 minutes) in the designated fragment chromatographic traces 300A, 300B, 300C.

The analysis engine 14 may then determine a retention time for the analyte parameter set 202', and correspondingly for the designated precursor ion 204' (Block 522). Typically, the engine 14 determines the retention time by detecting a dominant peak 410 in the combined chromatographic trace 400. Since all designated fragments (eg. 206A, 206B, 206C) in an analyte parameter set (eg. 202') should share the same retention time (and should hence have a non-zero intensity value in each designated fragment chromatographic trace 300A, 300B, 300C), by multiplying the data point values in the traces (eg. 300A, 300B, 300C) together, it is expected that the largest value/dominant peak corresponds to the retention time.

Thus for example, as can be seen by referring to the peak 310A (at 23.03 minutes) in FIG. 3A and the peak 410 in FIG. 4 (at 21.80 minutes), the peak 310A is misleading and reflects interfering matrix components. The corresponding value at 23.03 minutes in FIG. 4 (close to point 450 at 23.17 minutes) is close to zero.

The analysis engine 14 may then quantify the designated precursor ion 204' (Block 524). Typically, the engine 14 determines the quantity by integrating a dominant peak (eg. 310B, 310C) in a designated fragment chromatographic trace (eg. 300A, 300B, 300C), which corresponds to the determined retention time (determined in Block 522). Alternatively, quantitiation may be determined by integrating the dominant peak 410 in the combined chromatographic trace 400, as will be understood.

As will be understood, the controller 12 may generate a report identifying the determined retention time, one or more of the chromatographic traces 300A, 300B, 300C, 400, quantities of the various designated ions 204 and hence the presence or absence of the corresponding analytes of interest (Block 526).

Thus, while what is shown and described herein constitute preferred embodiments of the subject invention, it should be understood that various changes can be made without departing from the subject invention, the scope of which is defined in the appended claims.

The invention claimed is:

1. A system for analyzing analytes in a sample, comprising:
 (a) an ion source for emitting ions from the sample;
 (b) a mass spectrometer adapted to receive the ions from the ion source, wherein the mass spectrometer includes:
  (i) a first mass analyzer to select ions received from the ion source,
  (ii) an ion fragmenter configured to fragment ions received from the first mass analyzer,
  (iii) a second mass analyzer configured to select ion fragments received from the ion fragmenter, and
  (iv) at least one detector configured to detect ion fragments received from the second mass analyzer;
 (c) a controller operatively coupled to the mass spectrometer and configured to control the first mass analyzer to select for a designated ion of interest and to control the second mass analyzer to select for a designated ion fragment of interest;
 (d) data storage for storing at least one analyte parameter set, wherein each analyte parameter set includes:
  (i) a designated precursor ion,
  (ii) a plurality of designated ion fragments, and
  (iii) a retention time window;
 (e) wherein the controller is responsive to the analyte parameter set, and during the retention time window for each analyte parameter set the controller is configured to control the first mass analyzer to select for the corresponding designated precursor ion and to control the second mass analyzer to select for the corresponding designated ion fragments;
 (f) wherein the controller is configured to determine a chromatographic trace for a plurality of the designated ion fragments in the analyte parameter set and wherein the controller is configured to determine a combined chromatographic trace corresponding to a non-linear combination of a plurality of the designated ion fragment chromatographic traces.

2. The system as claimed in claim 1, wherein each designated ion fragment chromatographic trace comprises a plurality of data points, each data point corresponding to an intensity of ion fragments detected by the detector at a point in time, and wherein the controller is configured to determine the combined chromatographic trace for an analyte parameter set by, for each point in time during the corresponding retention time window, multiplying the values of each corresponding data point in each designated ion fragment chromatographic trace in the combination.

3. The system as claimed in claim 1, wherein the controller is configured to determine a retention time corresponding to the analyte parameter set.

4. The system as claimed in claim 3, wherein the controller is configured to detect a dominant peak in the combined chromatographic trace, and wherein the determined retention time is selected to correspond to the dominant peak.

5. The system as claimed in claim 4, wherein the controller is configured to integrate a peak from at least one designated chromatographic trace, the peak corresponding to the determined retention time.

6. The system as claimed in claim 1, further comprising data storage operatively coupled to the controller, wherein the data storage is configured to store data corresponding to the ion fragments detected by the detector.

7. The system as claimed in claim 1, wherein the ion source is operatively coupled to a liquid chromatograph.

8. A system for analyzing ions emitted from an ion source, the system comprising:
   (a) a first mass analyzer adapted to receive and to select ions from the ion source,
   (b) an ion fragmenter configured to fragment ions received from the first mass analyzer,
   (c) a second mass analyzer configured to select ion fragments received from the ion fragmenter, and
   (d) a detector configured to detect ion fragments received from the second mass analyzer;
   (e) a controller operatively coupled to the first and second mass analyzers, to the fragmenter and to the detector, wherein the controller is configured to control the first mass analyzer to analyzer for a designated ion of interest and to control the second mass analyzer to select for a designated ion fragment of interest;
   (f) at least one analyte parameter set, wherein each analyte parameter set includes:
      (i) a designated precursor ion,
      (ii) a plurality of designated ion fragments, and
      (iii) a retention time window;
   (g) wherein the controller is responsive to the analyte parameter set, and during the retention time window for each analyte parameter set the controller is configured to control the first mass analyzer to select for the corresponding designated precursor ion and to control the second mass analyzer to select for the corresponding designated ion fragments;
   (h) wherein the controller is configured to determine a chromatographic trace for each designated ion fragment in the analyte parameter set and wherein the controller is configured to determine a combined chromatographic trace corresponding to a non-linear combination of a plurality of designated fragment chromatographic traces.

9. The system as claimed in claim 8, wherein each designated fragment chromatographic trace comprises a plurality of data points, each data point corresponding to an intensity of ion fragments detected by the detector at a point in time, and wherein the controller is configured to determine the combined chromatographic trace for an analyte parameter set by, for each point in time, multiplying the values of each corresponding data point in each designated fragment chromatographic trace.

10. The system as claimed in claim 8, wherein the controller is configured to determine a retention time.

11. The system as claimed in claim 10, wherein the controller is configured to detect a dominant peak in the combined chromatographic trace, and wherein the determined retention time is selected to correspond to the dominant peak.

12. The system as claimed in claim 11, wherein the controller is configured to integrate a peak from at least one designated chromatographic trace, the peak corresponding to the determined retention time.

13. The system as claimed in claim 8, further comprising data storage operatively coupled to the controller, wherein the data storage is configured to store data corresponding to the ion fragments detected by the detector.

14. A method of analyzing a sample, comprising:
   (a) emitting ions from the sample;
   (b) selecting the emitted ions for a designated ion;
   (c) fragmenting the designated ions;
   (d) scanning for a plurality of designated ion fragments;
   (e) determining a designated fragment chromatographic trace for each designated ion fragment;
   (f) generating a combined chromatographic trace corresponding to a non-linear combination of a plurality of designated fragment chromatographic traces.

15. The method as claimed in claim 14, wherein step (f) comprises multiplying the designated fragment chromatographic traces together to generate the combined chromatographic trace.

16. The method as claimed in claim 15, further comprising:
   (g) determining a retention time.

17. The method as claimed in claim 16, further comprising generating a report containing data corresponding to the determined retention time.

18. The method as claimed in claim 16, wherein the determined retention time corresponds to a dominant peak in the combined chromatographic trace.

19. The method as claimed in claim 16, further comprising:
   (h) integrating a peak from at least one designated chromatographic trace, the peak corresponding to the determined retention time.

20. The method as claimed in claim 14, wherein steps (b) through (d) are performed during a predetermined retention time window.

21. The method as claimed in claim 20, wherein the retention time window is selected to correspond to a time period when the designated ion is expected to be emitted from the sample.

22. The method as claimed in claim 14, wherein steps (b) through (f) are performed for a plurality of different designated ions during a plurality of retention time windows, each retention time window corresponding to a designated ion.

23. The method as claimed in claim 22, wherein each retention time window is selected to correspond to a time period when the corresponding designated ion is expected to be emitted from the sample.

24. Computer readable media configured to cause a mass spectrometer having a computer controller to perform the method of claim 14.

* * * * *